US005723503A

United States Patent [19]
Smith et al.

[11] Patent Number: 5,723,503
[45] Date of Patent: *Mar. 3, 1998

[54] BIOLOGICAL TREATMENT FOR RHEUMATOID ARTHRITIS

[75] Inventors: J. Bruce Smith; John G. Fort, both of Philadelphia, Pa.

[73] Assignee: Thomas Jefferson University, Philadelphia, Pa.

[*] Notice: The term of this patent shall not extend beyond the expiration date of Pat. No. 5,674,487.

[21] Appl. No.: 314,156

[22] Filed: Sep. 28, 1994

[51] Int. Cl.$^6$ ............................................. A06N 63/00
[52] U.S. Cl. ................ 514/825; 424/93.1; 424/93.71; 424/534
[58] Field of Search ................ 514/825; 424/93.1, 424/93.71, 534

[56] References Cited

U.S. PATENT DOCUMENTS

| | | | |
|---|---|---|---|
| 4,996,194 | 2/1991 | Cohen et al. | 514/21 |
| 5,114,721 | 5/1992 | Cohen et al. | 424/534 |
| 5,239,062 | 8/1993 | Blattler et al. | 530/396 |
| 5,304,474 | 4/1994 | Lipsky et al. | 435/101 |
| 5,316,763 | 5/1994 | Ochoa et al. | 424/85.2 |

OTHER PUBLICATIONS

Elliott et al., "Treatment of Rheumatoid Arthritis with Chimeric Monoclonal Antibodies to Tumor Necrosis Factor α." *Arthritis Rheum.*, 36:1681–1690, 1993.

Goldberg et al., "Immunological Effects of High Dose Administration of Anti–CD4 Antibody in Rheumatoid Arthritis Patients." *J. Autoimmun.*, 4:617–630, 1991.

Herzog et al., "Anti–CD4 Antibody Treatment of Patients with Rheumatoid Arthritis: I. Effect on Clinical Course and Circulating T Cells." *J. Autoimmun.*, 2:627–642, 1989.

Horneff et al., "Treatment of Rheumatoid Arthritis with an Anti–CD4 Monoclonal Antibody." *Arthritis Rheum.*, 34:129–140, 1991.

Karsh et al., "Lymphapheresis in Rheumatoid Arthritis." *Arthritis Rheum.*, 24:867–873, 1981.

Kingsley et al., "T Cell Vaccination in Humans." *Clinical & Exp. Rheum.*, 11 (suppl. 8):S63–S64, 1993.

Lohse et al., "Induction of an Anti–vaccine Response by T Cell Vaccination in Non–human Primates and Humans." *J. Autoimmun.*, 1:121–130, 1993.

Moreland et al., "Use of a Chimeric Monoclonal Anti–CD4 Antibody in Patients with Refractory Rheumatoid Arthritis." *Arthritis Rheum.*, 36:307–318, 1993.

Nelson et al., "Maternal–Fetal Disparity in HLA Class II Alloantigens and the Pregnancy–Induced Amelioration of Rheumatoid Arthritis." *N. Engl. J. Med.*, 329:466–471, 1993.

Paulus et al., "Lymphocyte Involvement in Rheumatoid Arthritis." *Arthritis Rheum*, 20:1249–1262, 1977.

Persellin, R.H., "The Effect of Pregnancy on Rheumatoid Arthritis." *Bul. Rheum. Dis*, 27:922–927, 1977.

Reiter et al., "Treatment of Rheumatoid Arthritis with Monoclonal CD4 Antibody M–T151." *Arthritis Rheum.*, 34:525–536, 1991.

Sany et al., "Immunomodulating Effect of Human Placenta–Eluted Gamma Globulins in Rheumatoid Arthritis." *Arthritis Rheum.*, 25:17–24, 1982.

Strand et al., "Effects of Administration of An Anti–CD5 Plus Immunoconjugate in Rheumatoid Arthritis." *Arthritis Rheum.*, 36:620–630, 1993.

Trentham et al., "Clinical and Immunologic Effects of Fractionated Total Lymphoid Irradiation in Refractory Rheumatoid Arthritis." *N. Eng. J. Med.*, 305:976–982, 1981.

Tumiati et al., "High–Dose Immunoglobulin Therapy as an Immunomodulatory Treatment of Rheumatoid Arthritis." *Arthritis Rheum.*, 35:1126–1133, 1992.

van Laar et al., "Effects of Inoculation with Attenuated Autologous T Cells in Patients with Rheumatoid Arthritis" *J. Autoimmun.*, 6:159–167, 1993.

Wallace et al., "Plasmaphersis and Lymphoplasmapheresis in the Management of Rheumatoid Arthritis." *Arthritis Rheum.*, 22:703–710, 1979.

*Primary Examiner*—James J. Seidleck
*Assistant Examiner*—Michael A. Williamson
*Attorney, Agent, or Firm*—Law Offices of Jane Massey Licata

[57] ABSTRACT

A method of treating rheumatoid arthritis is provided which involves administering an effective amount of allogeneic mononuclear cells or a molecule derived from these cells to an individual having rheumatoid arthritis. Also provided are compositions for the treatment of rheumatoid arthritis.

5 Claims, No Drawings

BIOLOGICAL TREATMENT FOR RHEUMATOID ARTHRITIS

BACKGROUND OF THE INVENTION

Tens of millions of people in the United States suffer from rheumatoid arthritis (RA) or a related disease. While arthritis results in significantly fewer deaths as compared to cancer and cardiovascular diseases, there is no other group of diseases that causes so much suffering in so many people for such a prolonged period of time. Because of the tendency to disable and even permanently cripple individuals suffering from arthritis, this group of diseases is extremely important both socially and economically. There is presently no satisfactory cure for rheumatoid arthritis because its cause is unknown. In addition, many of the therapeutic agents administered to alleviate pain and inflammation associated with the disease, such as disease-modifying antirheumatic drugs (DMARDs) and non-steroidal anti-inflammatory agents (NSAIDs), produce intolerable side effects.

The understanding of the RA disease process has been considerably enhanced by the application of molecular immunology techniques. It is now generally accepted that rheumatoid arthritis represents a multifactorial disease with environmental factors (infectious agents or toxins), genetic susceptibility, and immune or autoimmune responses playing inter-connected roles. After initiation of the disease process, it is believed that activated T cells and their products are responsible for the progressive destruction of articular cartilage and sub-chondral bone that is characteristic of rheumatoid arthritis.

Advances in the understanding of the immunopathogenesis of rheumatoid arthritis have been coupled with immunologic strategies for treatment. Immunologic approaches to the treatment of rheumatoid arthritis are important and desirable given the potential toxicities associated with most remittive therapy in use today and the continued poor prognosis of rheumatoid arthritis despite aggressive drug treatment.

Monoclonal anti CD4 antibodies have been used in the treatment of rheumatoid arthritis (Reiter et al., *Arthritis Rheum.* 1991, 34, 525–536; Horneff et al., *Arthritis Rheum.* 1991, 34, 129–140; Herzog et al., *J. Autoimmunity* 1989, 2, 627–642; Goldberg et al., *J. Autoimmunity* 1991, 4, 617–630). In these studies, involving approximately 30 patients, objective and subjective improvement was noted in nearly all cases.

Another study employed chimeric monoclonal antibody to CD4 to treat 25 patients with refractory rheumatoid arthritis (Moreland et al., *Arthritis Rheum.* 1993, 36, 307–318) and again, some beneficial effects were observed.

Immunotherapeutic approaches have also included leukapheresis, (Karsh et al., *Arthritis Rheum.* 1981, 24, 867–873; Wallace et al., *Arthritis Rheum.* 1979, 22, 703–710) thoracic duct drainage (Paulus et al., *Arthritis Rheum.* 1977, 20, 1249–1262) and total node irradiation (Trentham et al., *N. Engl. J. Mad.* 1981, 305, 976–982). All of these modalities have resulted in varying degrees of improvement, but all also have obvious drawbacks.

Patients with rheumatoid arthritis have also been treated with one or more 5 day infusion courses with monoclonal anti-CD5 coupled to Ricin-A chain (Strand et al., *Arthritis Rheum.* 1993, 36, 620–630). In this open-label trial, improvement rates were 50–68% at one month and 22–25% at 6 months (two clinical trials were included). All patients produced antibodies against the anti-CD5 conjugate and most experienced a transient decrease in CD3/CD5 positive T cells with recovery after 2–4 weeks.

Since cytokines also play important pathophysiologic roles in rheumatoid arthritis, research into therapeutics has also focused in this area. Tumor necrosis factor (TNFα) has received attention because it is consistently found in synovium of patients suffering from rheumatoid arthritis. In addition, anti-human TNF was demonstrated to prevent the development of arthritis in a transgenic human TNFα mouse model. Elliott et al. (*Arthritis Rheum.* 1993, 36, 1681–1690) used chimeric (mouse-human) antibodies to TNFα to treat twenty patients with active rheumatoid arthritis. Patients were given 20 mg/kg in divided doses weekly either over 2 or 4 weeks. They found overall improvement in the Ritchie Articular Index, joint count and C-reactive protein (CRP) levels, and reported no significant toxicity.

Immunization of patients having rheumatoid arthritis with autologous T cell lines established from cells obtained from RA synovial fluid (SF) and/or synovial tissue has also been shown to be of benefit in some patients (Kingsley and Verwilghen, *Clin. Exp. Rheumatol.* 1993, 11, S63–S64; Lohse et al., *J. Autoimmunity* 1993, 1, 121–130; vanLaar et al., *J. Autoimmunity* 1993, 6, 159–167).

Regarding treatment of humans with allogeneic mononuclear cells (MNC), patients receiving living-related renal transplants have been transferred with allogeneic blood in an attempt to limit the immune response. Similar therapies employing MNC have been applied in recurrent pregnancy loss since about 1981 based on the notion that the fetus represents an allogeneic "graft" and that women who have no demonstrable known cause for recurrent spontaneous abortion (RSA) are likely to be immunologically rejecting their fetuses. Since 1985, the inventor has immunized over 1500 women diagnosed as having RSA with MNC from their spouses. World-wide it is estimated that about 25,000 patients have received this treatment. No serious side effects from this treatment have been found.

Remission of rheumatoid arthritis occurs in about 70% of all pregnant women suffering from rheumatoid arthritis. Pregnancy induced remission was originally believed to be due to increased levels of cortisol but, clearly, it is not entirely due to hormonal effects. It has been observed that during pregnancy, women with rheumatoid arthritis who experience remission carry fetuses that are more disparate than similar to themselves with respect to class II alleles of the human leukocyte antigens HLA-DRB1, -DQA and -DQB (Nelson et al., *N. Eng. J. Med.* 1993, 329, 466–471). The immunologic mechanism(s) underlying this effect is not known; however, hypotheses include induction of suppressor mechanisms or displacement of arthritogenic peptides from maternal antigen presenting cells (APC) by fetal class II peptides thus subverting an arthritis-inducing immune response. Alternatively, maternal T cell recognition of specific allogeneic or fetal HLA-DR peptides may cause a switch from a predominantly proinflammatory response to one that is protective or suppressive.

The known phenomenon of pregnancy-induced remission and post partum exacerbation of rheumatoid arthritis (Persellin, RH, *Bull. Rheum. Dis.* 1976, 77, 922–927) led to the use of gamma globulin eluted from placentas in the treatment of rheumatoid arthritis. In one study, 11 patients were treated with placenta-eluted gamma globulin and improvement was noted in seven of these patients (Sany et al., *Arthritis Rheum.* 1982, 25, 17–24). High dose intravenous immunoglobulin (IVGG) has also been shown to be effective in modulating the course of rheumatoid arthritis (Tumiati et al., *Arthritis Rheum.* 1992, 35, 1126–1133). Ten patients with active, severe rheumatoid arthritis were treated with 6 monthly infusions. All patients showed improvement, however, all patients also relapsed within weeks of the last infusion.

It has now been found that treatment of patients with active rheumatoid arthritis by immunization with allogeneic MNC can result in amelioration of symptoms and improvement in disease activity indices. This treatment approach was taken in order to determine if the beneficial effects of pregnancy on rheumatoid arthritis could be duplicated in non-pregnant patients.

SUMMARY OF THE INVENTION

An object of the present invention is to provide a method of treating rheumatoid arthritis which comprises administering an effective amount of allogeneic mononuclear cells or molecules derived from these cells to an individual having rheumatoid arthritis.

Another object of the present invention is to provide a composition for the treatment of rheumatoid arthritis comprising purified allogeneic white blood cells or molecules derived from these cells.

DETAILED DESCRIPTION OF THE INVENTION

Administration of an effective amount of allogeneic white blood cells or molecules derived from these cells can be used to treat patients suffering from rheumatoid arthritis. Approximately 80 to 100 million cells administered in a standard buffered salt solution (Lactated Ringers solution) to a patient suffering from rheumatoid arthritis at 6–8 week intervals has been found to be an effective amount, alleviating patient suffering. By "effective amount" it is meant a concentration of allogeneic mononuclear cells or molecules derived from these cells which, when administered to a patient suffering from rheumatoid arthritis, produce a beneficial effect.

Allogeneic MNC has been administered to 6 female patients with active rheumatoid arthritis. In each instance, MNC were obtained from the patient's spouse or an individual chosen by the patient. In this first trial, patients received a series of at least 3 injections of approximately $10^8$ MNC at 6 week intervals. No adverse effects were noted in any of the patients. Clear improvement occurred in 5 of 6 patients. Table 1 shows results of Arthritis Impact Measurement Scales (AIMS) scores, which provides a numerical means of following disease activity, physician global assessments, patient assessment of pain, swollen joint counts, and erythrocyte sedimentation rate (ESR) and/or C-reactive protein (CRP) determination on all patients entered.

TABLE 1

Measure of Disease Activity in Patients
in the Preliminary Trial of Allogeneic
Mononuclear Cell Immunization for Rheumatoid Arthritis

| Pa-tient | Pre-trial data and MNC Rx | ESR or CRP | Physician Global Assess. | Patient Assess. of Pain | AIMS score | Swollen Joint Count |
|---|---|---|---|---|---|---|
| S.M. | Prelim. data | 40 mm/hr. | 59 | 67 | | 11 |
| | Immuniz. #1 | 50 | | | 37.36 | |
| | Immuniz. #2 | 39 | 40 | 68 | 44.15 | 8 |
| | Immuniz. #3 | 28 | 18 | 22 | 20.58 | 4 |
| R.E. | Prelim. data | | | 49 | 67 | | 9 |
| | Immuniz. #1 | 2.49 mg/dl | 88 | 81 | 55.35 | 12 |
| | Immuniz. #2 | 5.43 | 53 | 90 | 59.12 | 10 |
| | Immuniz. #3 | 2.53 | 47 | 45 | 45.87 | 8 |
| J.B. | Prelim. data | | | 43 | 25 | | 8 |
| | Immuniz. #1 | 50 mm/hr | | | 53.06 | |

TABLE 1-continued

Measure of Disease Activity in Patients
in the Preliminary Trial of Allogeneic
Mononuclear Cell Immunization for Rheumatoid Arthritis

| Pa-tient | Pre-trial data and MNC Rx | ESR or CRP | Physician Global Assess. | Patient Assess. of Pain | AIMS score | Swollen Joint Count |
|---|---|---|---|---|---|---|
| | Immuniz. #2 | 66 | 27 | 16 | 37.38 | 11 |
| | Immuniz. #3 | 47 | 16 | 30 | 36.09 | 4 |
| L.C. | Prelim. data | 34 mm/hr | 61 | 39 | 45.64 | 14 |
| | Immuniz. #1 | | 51 | 42 | 41.60 | 12 |
| | Immuniz. #2 | | 21 | 10 | 34.90 | 12 |
| | Immuniz. #3 | 21 | 23 | 17 | 27.94 | 6 |
| R.H. | Prelim. data | 16 mm/hr | 30 | 29 | 42.78 | 7 |
| | Immuniz. #1 | 10 | 35 | 36 | 30.52 | 14 |
| | Immuniz. #2 | 15 | 20 | 2 | 21.57 | 4 |
| | Immuniz. #3 | 31 | 25 | 52 | 32.86 | 12 |
| W.V. | Prelim. data | 6 mm/hr | | | | |
| | Immuniz. #1 | 8 | 58 | 78 | 65.71 | 8 |
| | Immuniz. #2 | 9 | 62 | 85 | NA | 7 |
| | Immuniz. #3 | 9 | 34 | 78 | 73.21 | 8 |

A summary of clinical disease activity assessments on the six patients who have completed a series of three MNC treatments at 6 week intervals is provided in Table 2. Each separate analysis revealed statistically significant improvement at 95% confidence (paired Student's test).

TABLE 2

Mean Values of Disease Activity Measurements
in Six Patients Before and After Completing
Three MNC Immunizations for Rheumatoid Arthritis

| | AIMS Score | Physician Global Assess. | Patient Assess. of Pain | Swollen Joint Count |
|---|---|---|---|---|
| Before | 49.98 | 50.00 | 54.80 | 11.3 |
| After | 34.43 | 27.17 | 40.67 | 6.8 |
| p Value | <.001 | <.001 | <.001 | <.001 |

It may be that class II major histocompatability (MHC) gene products are responsible for the beneficial effect in RA observed after MNC treatment, just as it is class II disparity between a mother an fetus that appears to induce pregnancy-associated remission of RA. The genes of the major histocompatibility complex direct the synthesis of proteins that can be found on the surfaces of most cells. These proteins are referred to as the human leukocyte antigens (HLA) or sometimes as "MHC determinants" HLA are molecules that determine individuality within a species, bind and present antigens to immunecompetent cells, and are targets of graft rejection by immune effector cells. Thus, HLA are both necessary for immune responses to occur in individuals and can be targets of immune responses. HLA can bind an individual's own proteins and present these to the immune system. In some individuals this may result in autoimmune disease. MHC genes also determine susceptibility to certain diseases, for example, rheumatoid arthritis. HLA are designated class I or class II, based on their structure. Class I HLA are comprised of a single transmembrane alpha chain associated with beta-2 macroglobulin (β-2 m) and usually interact with CD8+ cytotoxic T cells. Class II HLA have both alpha and beta transmembrane heavy chains and interact with CD4+ T cells that mediate helper and inducer effects and delayed-type hypersensitivity which is the classical histopathology of RA. Class I HLA antigens are present on virtually all nucleated cells in the body and are highly expressed on cells of the immune system. Class II HLA antigens are restricted in their distribution and are found predominantly on certain cells of the immune system. Relevant to the present invention, T cells express only class I antigens while B lymphocytes and monocytes express both class I and II antigens. These types of cells can be isolated from each other by depleting one or the other groups of cells thereby providing two sets of cells for comparison in immunization procedures. MNC prepared form whole blood contain T cells, B cells and monocytes. Only T cells remain when MNC is treated with an antibody directed against class II HLA antigens. An example of such an antibody is the monoclonal antibody known as L243. Only B cells and monocytes remain if MNC is treated with a monoclonal antibody that only reacts with T cells. Anti CD3 is one example of such an antibody.

Patients suffering from rheumatoid arthritis may be treated with whole MNC populations (containing monocytes, B cells and T cells) or a sub-population of MNC. Either the population of B cells plus monocytes (positive for both class I and class II MLA molecules or the population of T cells (positive for class I but not class II HLA) are believed to mediate the effects. There are several means by which these cells can be effectively separated from each other which are routine to those of skill in the art including, but not limited to, magnetic cell sorting that employs a device and reagents manufactured by Immunicon Corp. (Reg) Huntington Valley, Pa. In one embodiment, MNC are treated with formalin to increase antigenicity of the cells and negate the possibility of these cells causing graft vs. host disease in an immunocompromised individual.

It is also believed that a beneficial effect can also result from the treatment of patients suffering from rheumatoid arthritis with purified class I or class II molecules. Presentation of these molecules on the allogeneic cell surface is not required. Thus, compositions comprising purified class I and/or class II HLA molecules from single, selected or pooled donor white blood cells; portions of class I and/or II molecules (attenuated molecules or peptides) fractionated from whole molecule preparations; and synthetically prepared peptides or larger molecules based on the knowledge of amino acid sequence and structure studies of the class I or II molecules may be administered.

In a preferred embodiment, compositions of the present invention which contain molecules as described above are presented to the patient using whole blood as a vehicle. For example, cells of specifically identified donors or the patient's own cells which are obtained, treated with the composition and reinjected into the patient, can be used. The composition can be attached to the blood cells in a number of ways, including chemical attachment of the relevant product to the patients red blood cells, and attachment of the relevant product to the patients white blood cells. In a preferred embodiment monocytes are used, as these cells have the capability of binding the class I or class II molecules/peptides as one of their normal functions. The procedures required to produce compositions of the present invention are routine to an individual skilled in the arts of immunology and molecular biology/chemistry.

The following examples are provided for illustrative purposes only and are not intended to limit the invention in any way.

EXAMPLES

Example 1

Patient Profiles and Disease Assessment

Six patients were treated in the first trial. None of the patients were receiving concomitant treatment with disease modifying anti-rheumatic drugs (DMARDs), and only one was receiving a small dose of prednisone (<10 mg/day). If patients were taking DMARDs, this treatment was discontinued for 6 weeks prior to entry into the immunotherapy trial. Disease activity was assessed clinically by patient global assessment of pain, physician global assessment of disease activity, AIMS questionnaire and swollen joint counts. Laboratory assessment included hematologic profile with platelet counts, erythrocyte sedimentation rate (ESR) and/or C-reactive protein determination (CRP). These parameters were recorded prior to entry into the study and 6 weeks thereafter including 6 weeks after the last injection of MNC in 2 patients and 9 months after the last injection in one patient. The latter patient has had no recurrence of active rheumatoid arthritis, the other two patients had evidence of active rheumatoid arthritis 6 weeks after the last injections. One of those patients, JB, improved after immunotherapy was reinstituted.

Example 2

Isolation of MNC

In each instance MNC were obtained from the patient's spouse or an individual chosen by the patient. MNC donors were screened for liver enzyme abnormalities, hepatitis B and C, human immunodeficiency viruses 1 (HIV-1) and 2 (HIV-2) and human T lymphotropic virus 2 (HTLV-2). Blood (100–120 ml) was obtained from the donors by venipuncture. This amount of blood usually yields between 80 and $150 \times 10^6$ MNC after ficol-hypaque centrifugation. After washing in Earle's balanced salt solution, MNC were resuspended in 4 ml lactated Ringer's solution. Two ml were injected intravenously (IV) and the remaining 2 ml in divided doses of 0.5 ml each subcutaneously (SQ), at 4–6 week intervals. This treatment resulted in statistically significant improvement in the rheumatoid arthritis in 5 of 6 patients who received three treatments after immunotherapy was instituted.

Example 3

Treatment Protocol in Larger Clinical Trials

Patients are divided into two groups, each group receiving a series of six treatments by intravenous bolus injection or subcutaneous injection. The patients in each group will be randomly assigned to receive different types of MNC. The randomization assignment is accomplished by a computer program so that by chance alone a patient will receive either MNC that are all positive for only class I HLA antigens (T cells) or MNC that are all positive for both class I and class II HLA antigens (B cells and monocytes). Immunizations will be performed at 6 week intervals using $80-100 \times 10^6$ cells each time. Patients in whom a beneficial effect is seen after 6 injections, are treated on a continuing basis but with graduated (2 weeks) lengthening of the interval between injections in order to determine the maximum time period that can elapse between treatments.

Example 4

Criteria for Assessing Clinical Outcome

Clinical outcomes are assessed using the American College of Rheumatology (ACR) core criteria for disease activity. Six of these criteria are applied prior to study entry and at 6 week intervals during and for up to 12 weeks after completion of the trial. The criteria include swollen joint count, AIMS score, physician global assessment of disease activity (10 cm analog scale), patient assessment of pain (10 cm analog scale) and acute phase reactant value (ESR and/or CRP).

Example 5

Collection of MNC

When donor screening tests are complete, donors are scheduled with the TJU Blood Donor Center for obtaining a "buffy coat". MNC (300–500×10$^6$) are recovered from "buffy coats" by ficol hypaque centrifugation. For patients randomized to receive only class I positive cells, class II positive cells are depleted using supernatants of the L243 anti HLA-DR hybridoma cell line which is well known in the art. Patients randomized to receive class I and II positive cells receive cells magnetically depleted of CD3+ MNC. Cells prepared for immunization are labeled and stored in liquid nitrogen in 90% fetal calf serum (FCS)/10% dimethyl sulfoxide (DMSO) until used for patient treatment. Greater than 90% of cells frozen in this manner are recovered.

What is claimed:

1. A method of treating rheumatoid arthritis comprising administering an effective amount of allogeneic mononuclear cells obtained from a human donor to an individual having rheumatoid arthritis.

2. The method of claim 1 wherein the cells comprise B cells.

3. The method of claim 1 wherein the cells comprise monocytes.

4. The method of claim 1 wherein the cells comprise T cells.

5. A method of treating rheumatoid arthritis comprising administering to an individual having rheumatoid arthritis an effective amount of allogeneic mononuclear cells obtained from a human donor wherein the cells have been treated with formalin.

* * * * *

UNITED STATES PATENT AND TRADEMARK OFFICE
CERTIFICATE OF CORRECTION

PATENT NO. : 5,723,503

DATED : March 3, 1998

INVENTOR(S) : Smith et al.

It is certified that error appears in the above-indentified patent and that said Letters Patent is hereby corrected as shown below:

At col 1, line 56, please delete "Mad." and insert therefor --Med.--.

At col 4, line 50, please delete "immunecompetent" and insert therefor --immunocompetent--.

Signed and Sealed this

Twenty-sixth Day of May, 1998

Attest:

BRUCE LEHMAN

*Attesting Officer*     *Commissioner of Patents and Trademarks*